United States Patent
Elmouelhi et al.

(10) Patent No.: US 9,186,207 B2
(45) Date of Patent: Nov. 17, 2015

(54) DISTAL VIEWING WINDOW OF A MEDICAL CATHETER

(75) Inventors: Ahmed Elmouelhi, Minneapolis, MN (US); Gareth Morgan, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 2189 days.

(21) Appl. No.: 11/818,391

(22) Filed: Jun. 14, 2007

(65) Prior Publication Data

US 2008/0312497 A1    Dec. 18, 2008

(51) Int. Cl.
| | |
|---|---|
| A61B 1/00 | (2006.01) |
| A61B 1/04 | (2006.01) |
| A61B 1/06 | (2006.01) |
| A61B 18/04 | (2006.01) |
| A61B 18/14 | (2006.01) |
| A61B 1/307 | (2006.01) |
| A61B 18/00 | (2006.01) |

(52) U.S. Cl.
CPC ............ *A61B 18/1477* (2013.01); *A61B 1/307* (2013.01); *A61B 18/1492* (2013.01); *A61B 2018/00547* (2013.01); *A61B 2018/00577* (2013.01); *A61B 2018/00982* (2013.01); *A61B 2018/1475* (2013.01); *A61B 2218/002* (2013.01)

(58) Field of Classification Search
USPC .............. 600/104, 114, 160–179, 106, 107; 600/128–130; 606/32–51, 139–147
See application file for complete search history.

(56) References Cited

U.S. PATENT DOCUMENTS

| | | | |
|---|---|---|---|
| 5,435,805 A | 7/1995 | Edwards et al. |
| 5,454,782 A | 10/1995 | Perkins |
| 5,458,597 A | 10/1995 | Edwards et al. |
| 5,470,308 A | 11/1995 | Edwards et al. |
| 5,472,441 A | 12/1995 | Edwards et al. |
| 5,507,743 A | 4/1996 | Edwards et al. |
| 5,531,676 A | 7/1996 | Edwards et al. |

(Continued)

FOREIGN PATENT DOCUMENTS

| | | |
|---|---|---|
| EP | 1 402 837 A1 | 3/2004 |
| EP | 1 543 780 B1 | 11/2006 |

(Continued)

OTHER PUBLICATIONS

Birch et al., "Transurethral Resection of Prostate Under Sedation and Local Anesthesia (Sedoanalgesia)," Urology, Aug. 1991 vol XXXVIII, No. 2., pp. 113-118.

(Continued)

*Primary Examiner* — Ryan Henderson
(74) *Attorney, Agent, or Firm* — Shumaker & Sieffert, P.A.

(57) ABSTRACT

The disclosure describes an elongated housing, e.g., a catheter, configured to be inserted into a lumen of a patient to diagnose or treat a patient. The elongated housing includes a scope channel that accepts a cystoscope and a viewing window at the distal end of the elongated housing. The user may use the cystoscope to view tissue adjacent to the viewing window. The viewing window may take up at least 10 percent of the length of the elongated housing to allow the user to identify a large area of tissue in the lumen without moving the elongated housing with respect to the tissue. Once the user identifies the target tissue, the user may position the elongated housing graduations on the viewing window and the proximal end of the elongated housing. An ablation needle electrode may be extended into the target tissue to deliver ablation therapy to the target tissue.

25 Claims, 8 Drawing Sheets

(56) References Cited

U.S. PATENT DOCUMENTS

| | | | |
|---|---|---|---|
| 5,536,267 A | | 7/1996 | Edwards et al. |
| 5,749,846 A | | 5/1998 | Edwards et al. |
| 5,755,714 A | * | 5/1998 | Murphy-Chutorian ......... 606/15 |
| 5,855,577 A | * | 1/1999 | Murphy-Chutorian et al. .. 606/7 |
| 5,865,788 A | | 2/1999 | Edwards et al. |
| 5,964,756 A | | 10/1999 | McGaffigan et al. |
| 5,995,875 A | | 11/1999 | Blewett et al. |
| 6,010,500 A | * | 1/2000 | Sherman et al. ................ 606/41 |
| 6,071,280 A | | 6/2000 | Edwards et al. |
| 6,090,105 A | | 7/2000 | Zepeda et al. |
| 6,106,521 A | | 8/2000 | Blewett et al. |
| 6,113,594 A | | 9/2000 | Savage |
| 6,113,597 A | | 9/2000 | Eggers et al. |
| 6,129,726 A | | 10/2000 | Edwards et al. |
| 6,231,591 B1 | | 5/2001 | Desai |
| 6,238,393 B1 | | 5/2001 | Mulier et al. |
| 6,241,702 B1 | | 6/2001 | Lundquist et al. |
| 6,302,903 B1 | | 10/2001 | Mulier et al. |
| 6,315,777 B1 | | 11/2001 | Comben |
| 6,327,492 B1 | | 12/2001 | Lemelson |
| 6,402,742 B1 | | 6/2002 | Blewett et al. |
| 6,409,722 B1 | | 6/2002 | Hoey et al. |
| 6,461,296 B1 | | 10/2002 | Desai |
| 6,464,661 B2 | | 10/2002 | Edwards et al. |
| 6,471,698 B1 | | 10/2002 | Edwards et al. |
| 6,497,705 B2 | | 12/2002 | Comben |
| 6,514,247 B1 | | 2/2003 | McGaffigan et al. |
| 6,526,320 B2 | | 2/2003 | Mitchell |
| 6,537,248 B2 | | 3/2003 | Mulier et al. |
| 6,537,272 B2 | | 3/2003 | Christopherson et al. |
| 6,551,300 B1 | | 4/2003 | McGaffigan |
| 6,623,515 B2 | | 9/2003 | Mulier et al. |
| 6,632,221 B1 | | 10/2003 | Edwards et al. |
| 6,632,222 B1 | | 10/2003 | Edwards et al. |
| 6,638,275 B1 | * | 10/2003 | McGaffigan et al. ........... 606/41 |
| 6,641,580 B1 | | 11/2003 | Edwards et al. |
| 6,652,516 B1 | | 11/2003 | Gough |
| 6,706,039 B2 | | 3/2004 | Mulier et al. |
| 6,761,715 B2 | | 7/2004 | Carroll |
| 6,814,712 B1 | | 11/2004 | Edwards et al. |
| 6,951,557 B2 | * | 10/2005 | Ellis et al. ....................... 606/15 |
| 6,989,004 B2 | | 1/2006 | Hinchliffe et al. |
| 2001/0031941 A1 | | 10/2001 | Edwards et al. |
| 2001/0039415 A1 | | 11/2001 | Francischelli et al. |
| 2002/0058933 A1 | | 5/2002 | Christopherson et al. |
| 2002/0111619 A1 | | 8/2002 | Keast et al. |
| 2002/0151884 A1 | | 10/2002 | Hoey et al. |
| 2002/0151888 A1 | * | 10/2002 | Edwards et al. ................ 606/41 |
| 2002/0177846 A1 | | 11/2002 | Mulier et al. |
| 2002/0183740 A1 | * | 12/2002 | Edwards et al. ................ 606/41 |
| 2002/0193851 A1 | * | 12/2002 | Silverman et al. ............ 607/101 |
| 2003/0028188 A1 | | 2/2003 | Paddock et al. |
| 2003/0073989 A1 | | 4/2003 | Hoey et al. |
| 2003/0103932 A1 | | 6/2003 | Slepian et al. |
| 2003/0212394 A1 | * | 11/2003 | Pearson et al. .................. 606/41 |
| 2004/0002647 A1 | | 1/2004 | Desai |
| 2004/0133194 A1 | | 7/2004 | Eum et al. |
| 2004/0172112 A1 | | 9/2004 | Cioanta et al. |
| 2005/0222562 A1 | * | 10/2005 | Lovewell ........................ 606/34 |
| 2006/0189845 A1 | * | 8/2006 | Maahs et al. .................. 600/146 |
| 2007/0077827 A1 | | 4/2007 | Bonde et al. |

FOREIGN PATENT DOCUMENTS

| | | |
|---|---|---|
| WO | WO 01/54567 A1 | 8/2001 |
| WO | WO 02/078557 A1 | 10/2002 |
| WO | WO 2006/096334 A2 | 9/2006 |

OTHER PUBLICATIONS

Leveillee et al., "Radiofrequency Interstitial Tissue Ablation: Wet Electrode," Journal of Endourology, vol. 17, No. 8, pp. 563-577, 2003.

Related patent application entitled "Delivery of Fluid During Transurethral Prostate Treatment", U.S. Appl. No. 10/424,040, filed Apr. 24, 2003, now abandoned.

Related patent application entitled "Bipolar Virtual Electrode for Transurethral Needle Ablation", U.S. Appl. No. 10/835,193, filed Apr. 29, 2004, now abandoned.

Notification of Transmittal of the International Search Report and the Written Opinion of the International Searching Authority, or the Declaration for corresponding patent application No. PCT/US2008/061160, mailed Sep. 26, 2008, 14 pages.

* cited by examiner

DISTAL VIEWING WINDOW OF A MEDICAL CATHETER

TECHNICAL FIELD

The invention relates to medical devices and, more particularly, to elongated housings that deliver therapy.

BACKGROUND

Medical catheters or elongated housings are used in a variety of procedures to diagnose or treat a patient at a location within the patient. A catheter typically has at least one channel that allows a device, medication, or apparatus to reach the desired location within the patient. Some catheters provide a channel that accepts a cystoscope, endoscope, or another image transmitting device so that the user can identify specific tissues or structures within the patient. Identification of a specific tissue via the catheter may be necessary in order to successfully deliver treatment to the desired tissue of the patient.

In one example, a catheter may be used to treat benign prostate hyperplasia (BPH) in men. BPH is a condition caused by the second period of continued prostate gland growth that constricts the urethra and may cause problems with urination and bladder functionality. Minimally invasive techniques for treating BPH include inserting a catheter into the urethra of the patient, identifying the prostate location, and extending a needle electrode from the catheter through the urethra and into the prostate tissue. The user delivers ablation therapy to the prostate via the needle electrode until ablation is complete. The user may reposition the catheter and extend the needle electrode into additional tissue sites until the patient has been treated. Once therapy is complete, the needle electrode is retracted into the catheter and the catheter is removed from the patient.

SUMMARY

The disclosure describes an elongated housing, e.g., a catheter, configured to be inserted into a lumen of a patient to diagnose or treat a patient. The elongated housing includes a scope channel that accepts a cystoscope and a distal viewing window at the distal end of the elongated housing. The distal viewing window is at least partially transparent so that the user can view tissue adjacent to the distal viewing window. In addition, the distal viewing window covers at least 10 percent of the elongated housing length in order to allow the user to view a substantial area of adjacent tissue without moving the elongated housing with respect to the surrounding lumen of the patient. The scope channel allows the user to slide the cystoscope axially to the desired location within the distal viewing window for viewing purposes. Graduations over the distal viewing window and the proximal end of the elongated housing may aid the user in positioning the elongated housing within the patient after identifying the target tissue through the distal viewing window.

In one embodiment, the disclosure is directed to a medical device that includes an elongated housing that defines a scope channel, a needle channel, and a distal viewing window. The distal viewing window is located near a distal end of the elongated housing, the distal viewing window is at least partially transparent and located along a window axial length and around a portion of a housing perimeter, and the window axial length is at least 10 percent of a housing length.

In another embodiment, the disclosure is directed to a system that includes a hand-held device having a lever actuated by a user and an elongated housing coupled to the hand-held device that defines a scope channel, a needle channel, and a distal viewing window. The distal viewing window is located near a distal end of the elongated housing, the distal viewing window is at least partially transparent and located along a window axial length and around a portion of a housing perimeter, and the window axial length is at least 10 percent of a housing length. The system also includes an ablation needle electrode that resides within the needle channel and exits out of a port in the distal viewing window in response to actuation of the lever.

In an alternative embodiment, the disclosure is directed to a method that includes inserting an elongated housing into a lumen of a patient, identifying a target tissue through the distal viewing window via the cystoscope, and moving a cystoscope axially within the scope channel. The elongated housing defines a scope channel, a needle channel, and a distal viewing window. The distal viewing window is located near a distal end of the elongated housing, the distal viewing window is at least partially transparent and located along a window axial length and around a portion of a housing perimeter, and the window axial length is at least 10 percent of a housing length.

In various embodiments, the catheter may provide one or more advantages. For example, the viewing window at the distal end of the elongated housing allows the user to move the cystoscope instead of the elongated housing to identify the target tissue within the lumen of the patient. Graduations over the viewing window that correspond to graduations at the proximal end of the elongated housing may also assist the user in quickly adjusting the position of the elongated housing. These features may reduce procedure time and patient pain associated with movement of the elongated housing. In addition, the elongated housing may allow the needle channel to slide within the elongated housing to position the ablation needle electrode without moving the elongated housing in the lumen of the patient.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
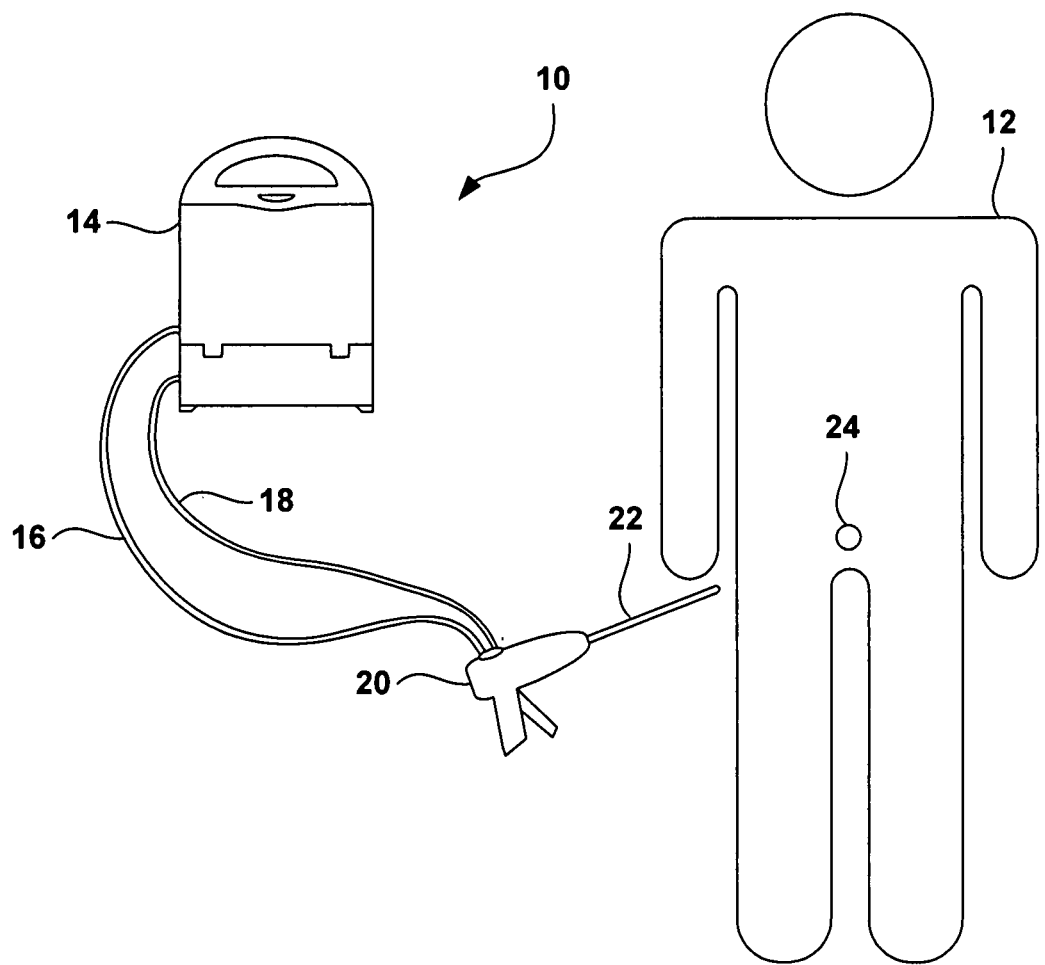
FIG. 1 is a conceptual diagram illustrating an exemplary hand-held device and elongated housing coupled to a generator for treating a patient.

Medical elongated housings, e.g., catheters, are commonly employed in a variety of applications that require the user, such as a clinician or physician, to access lumens within the patient. Elongated housings may allow diagnosis or treatment through minimally invasive procedures instead of major surgery. Specifically, an elongated housing may be configured for ablation therapy of prostate tissue. Benign prostate hyperplasia (BPH) is a condition caused by the second period of continued prostate gland growth that constricts the urethra and may cause problems with urination and bladder functionality. An elongated housing is used in minimally invasive techniques for treating BPH by inserting the elongated housing into the urethra of the patient to deliver ablation energy to the prostate while minimizing damage to other tissues. The user may use a cystoscope inserted within the elongated housing to view the urethra through the end of the elongated housing.

As described in more detail below, the elongated housing, e.g., a catheter, for delivering ablation therapy to the prostate includes a distal viewing window at the distal end of the elongated housing. The viewing window allows the user to view tissue along the length of the elongated housing that includes the viewing window. The viewing window, or window axial length, may be provided along at least 10 percent of the elongated housing length in order provide viewing access to a large area of tissue. In other words, the axial length of the distal viewing window may be of sufficient length to visualize the distance between multiple anatomical features within the body lumen of the patient. The user may desire to visualize any number of anatomical features necessary or beneficial to properly place the therapy delivered via the elongated housing.

In addition, the elongated housing may include graduations that aid the user in correctly positioning the elongated housing within the urethra. Graduations along the viewing window may correspond to graduations along the proximal end of the elongated housing so that the user can measure the distance to move the elongated housing and match the measurement to the graduations that the user can see outside of the urethra. These features may allow the user to easily identify the target tissue, reduce procedure time, and reduce the movement of the elongated housing with respect to the urethra. Overall, the elongated housing may decrease patient discomfort and recovery time.

The elongated housing described herein may be coupled to a hand-held device that the user holds on to during therapy. The hand-held device may include a trigger that extends and retracts the ablation needle electrode that resides within the elongated housing. The hand-held device may also be coupled to a signal generator that produces the ablation energy delivered to the patient via the ablation needle electrode. This system is described as being used for prostate ablation therapy. However, the system may be utilized for other ablation therapies within a patient or procedures that may benefit from a distal viewing window at the distal end of an elongated housing. Other features and examples of the elongated housing are described in more detail below.

FIG. 1 is a conceptual diagram illustrating an exemplary hand-held device and elongated housing coupled to a generator for treating a patient. As shown in FIG. 1, ablation system 10 may include a portable therapy delivery device (PTD) 14 that delivers therapy to treat a condition of patient 12. In this exemplary embodiment, PTD 14 is a radio frequency (RF) generator that provides RF energy to heat and ablate tissue of the prostate gland 24. This ablation of prostate tissue destroys a portion of the enlarged prostate caused by, for example, BPH. The RF energy is transmitted through electrical cable 16 to hand-held device 20. The energy is then transmitted through elongated housing 22, e.g., a catheter, and is delivered to prostate 24 by an ablation needle electrode (not shown). In addition to the ablation needle, a fluid may be pumped out of PTD 14, through tube 18, into hand-held device 20, and through elongated housing 22 to interact with the RF energy being delivered by the electrode. This wet electrode may increase the effective heating area of the electrode and increase therapy efficacy. Specifically, the effective heating area may be increased or decreased by changing the flow rate of fluid from PTD 14. Alternatively, the shape of the produced lesion may be changed by the type of delivered fluid from the wet electrode or shape and dimensions of the needle electrode. For example, cooled saline or a hypertonic fluid may be used to alter the generally spherical shape of the lesion.

In the illustrated example, PTD 14 includes an RF generator that includes circuitry for developing RF energy from an included rechargeable battery or drawn from a common electrical outlet. The RF energy is produced within defined ablation parameters to provide appropriate prostate tissue heating. PTD 14 also includes a user interface (not shown) that allows a user to control the ablation therapy when the screen of PTD is opened to show the user interface to the user.

Therapy energy and other associated functions such as fluid flow are controlled via the user interface located on a color liquid crystal display (LCD), or equivalent screen. The screen may provide images created by the therapy software, and the user may interact with the software by touching the screen at certain locations indicated by the user interface. In this embodiment, no additional devices, such as a keyboard or pointer device, are needed to interact with the device. The touch screen may also enable device operation.

The touchscreen of the user interface may be a liquid crystal display (LCD) touch screen. The physician may interact with the screen by using a finger or stylus to touch the screen where certain icons appear. In this manner, the physician may control the therapy and PTD operation without the use of additional keyboards or pointer devices. The screen may utilize any type of touch screen technology that allows the physician to select icons or graphics on the screen with a finger, stylus, or gloved finger. These types of technologies include, but are not limited to resistive systems, capacitive systems, and acoustic wave systems.

In some embodiments, the PTD 14 or hand-held device 20 may require an access code or biometric authorization to use the device. Requiring the physician to provide a fingerprint, for example, may limit unauthorized use of the system. In other embodiments, the user interface may include a pointing device, a keyboard, a joystick, or other input device. In alternative embodiments, the user interface may accept verbal commands from the user.

Connected to PTD 14 are one cable 16 and one tube 18. Cable 16 conveys RF energy and tube 18 conducts fluid from PTD 14 to hand-held device 20. Hand-held device 20 may include one or more triggers or levers to extend and retract one or more ablation needle electrodes residing within elongated housing 22. Hand-held device 20 may also include a button or lever that starts and stops RF energy and/or fluid from PTD 14 from being delivered to patient 12. Alternatively, these types of features may be enabled by the user interface of the PTD 14 instead of on hand-held device 20. Attached to the distal end of hand-held device 20 is elongated housing 22. Elongated housing 22 includes a scope channel and needle channel to position and deliver the therapy. In addition, elongated housing 22 may provide a conduit for the fluid and house and provide isolation between the one or more ablation needle electrodes within the needle channels that conduct RF energy to patient 12. Fluid may also or instead flow through the one or more ablation needle electrodes. Since elongated housing 22 would be entering patient 12 through the urethra, the elongated housing may be very thin in diameter and long enough to reach the prostate in any patient needing treatment.

Elongated housing 22 may contain the one or more ablation needle electrodes for delivering RF current to the tissue of enlarged prostate 24. The needle electrodes of elongated housing 22 may each penetrate into two areas of prostate 24 from the urethra. The two areas of prostate 24 penetrated by the needle electrodes may be adjacent to each other such that resulting lesions overlap or separated within prostate 24 such that the resulting lesions do not contact each other. When RF energy is being delivered, tissue will increase in temperature to destroy, i.e., ablate, a desired volume of tissue. This heating may last a few seconds or a few minutes, depending on the condition of prostate 24 and the desired size of the lesion formed from the ablation therapy. In some embodiments, the fluid may exit small holes in the needles and flow around the electrodes. In other embodiments, the fluid may enter the patient through a different mechanism than holes in the needles. For example, the fluid may pass through a permeable member, along a sheath, or via another element that distributes the fluid in a desired manner. Alternatively, a different elongated housing or needle than the electrode may deliver the fluid. This conducting fluid, e.g., saline, may increase the effective heating area and decrease the heating time. Additionally, ablating tissue in this manner may enable the physician to complete therapy without repositioning the needle or using different sized needles. In other examples, PTD 14 may provide ablation therapy without a conductive fluid. Instead, ablation therapy is achieved by one or more ablation needle electrodes that deliver energy directly to the tissue from the electrodes. However, fluid may still be used to cool surrounding tissue or clear debris from the treatment site.

In some cases, hand-held device 20 may only be used for one patient. Reuse may cause infection and contamination, so it may be desirable for the hand-held device to only be used once and then discarded. A feature on the hand-held device may be a smart chip in communication with PTD 14. The smart chip of the device may trigger the processor of PTD 14 to load a specific software application that utilizes the connected hand-hand device 20. As another example, when the hand-held device is connected to PTD 14, the PTD may request use information from hand-held device 20. If hand-held device 20 has been used before, PTD 14 may disable all functions of the hand-held device to prevent reuse of the device on a different patient. This determination may be presented to the user via the user interface as a warning or an error message. The user interface of PTD 14 may suggest a course of action for the user. Once hand-held device 20 has been used, the smart chip in the device may create a use log to identify the therapy delivered and record that the device has been used. The log may include data of RF energy delivered to patient 12, total RF energy delivered in terms of joules or time duration, error messages created, or any other pertinent information. In some embodiments, the user may utilize the user interface to modify the information stored in the log.

In some embodiments, additional peripheral accessories, i.e., therapy devices or diagnostic devices, may be available to the physician at one time. For example, hand-held device 20 for ablating prostate tissue might be coupled with an endoscopic camera for locating the prostate and monitoring therapy. The camera images may then be transferred back to PTD 14 and presented on the screen in real-time. Alternatively, the images from a cystoscope inserted into elongated housing 22 may be displayed on the screen of PTD 14. Other examples may include ultrasound imaging coupled with ablation therapy or programming implanted medical devices. The flexible platform of the PTD 14 may allow various diagnostic and therapy combinations to be combined into one device. In these cases, the user interface may be adapted to include these functions within the same delivery screen or require the user toggle between two or more screens to access control or to monitor the additional function.

While PTD 14 is described as a small portable device, the PTD could be embodied as any type of system that supports ablation therapy as described herein. For example, PTD 14 may be an RF generator controlled by a notebook computer. Alternatively, PTD 14 may be a large stationary ablation system that provides a large monitor on top of a stack of components of the system. In other embodiments, PTD 14 may only be the ablation component of a more comprehensive system that supports other functions or therapies separate from the ablation therapy. In any case, PTD 14 is only described herein as an exemplary embodiment of the ablation system which includes the user interface. Elongated housing 22 may be configured to be compatible with any variations of hand-held device 20 or PTD 14.

Figure 2:
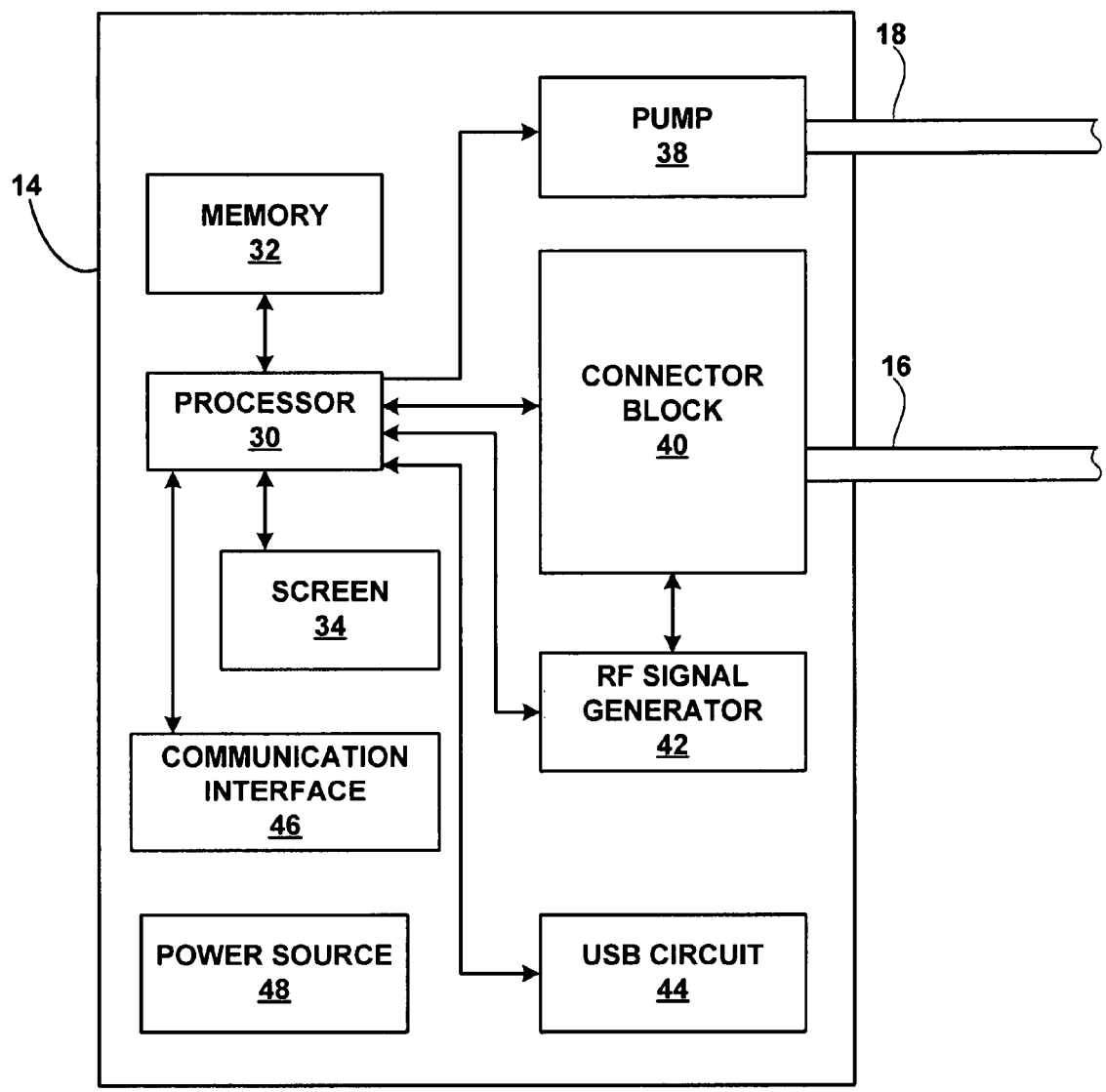
FIG. 2 is a block diagram of the generator that delivers therapy to the patient via the hand-held device and elongated housing.

FIG. 2 is a block diagram of the generator that delivers therapy to the patient via the hand-held device. As shown in FIG. 2, PTD 14 includes a processor 30, memory 32, screen 34, connector block 40, RF signal generator 42, pump 38, communication interface 46, USB circuit 44, and power source 48. As shown in FIG. 2, connector block 40 is coupled to cable 16 for delivering RF energy produced by RF signal generator 42. Pump 38 produces pressure to deliver fluid through tube 18.

Processor 30 controls RF signal generator 42 to deliver RF energy therapy through connector block 40 according to therapy parameter values stored in memory 32. Processor 30 may receive such parameter values from screen 34 or communication interface 46 or USB circuit 44. When signaled by the physician, which may be a signal from the hand-held device 20 conveyed through connector block 40, processor 30 communicates with RF signal generator 42 to produce the appropriate RF energy. As needed, pump 38 provides fluid to irrigate the ablation site or provides fluid to the electrode via elongated housing 22 during wet electrode ablation.

In a preferred embodiment, the RF signal generator may have certain performance parameters. In this exemplary case, the generator may provide RF energy into two delivery channels with a maximum of 50 Watts per channel. Other embodiments may include generation in excess of 100 watts for one channel. Duty cycles of the energy may alter the total power capable of being produced. In other examples, the ramp time for a 50 Watt change in power may occur in less than 25 milliseconds, and the output power may be selected in 1 Watt steps. The maximum current to be provided to the patient may be 2 Amps, and the maximum voltage may be 180 Volts. Other embodiments of the signal generator may have different power capabilities as needed by the intended use of PTD 14.

Connector block 40, e.g. connector board 46, may contain an interface for a plurality of connections, not just the connection for cable 16. These other connections may include one for a return electrode, a second RF energy channel, or a separate temperature sensor. As mentioned previously, connector block 40 may be a variety of blocks used to diagnose or treat a variety of diseases. All connector blocks may be exchanged and connect to processor 30 for proper operation. Pump 38 may be replaceable by the physician to replace a dysfunctional pump or use another pump capable of pumping fluid at a different flow rate.

Processor 30 may also control data flow from the therapy. Data such as RF energy produced, temperature of tissue, and fluid flow may be channeled into memory 32 for analysis. Processor 30 may comprise any one or more of a microprocessor, digital signal processor (DSP), application specific integrated circuit (ASIC), field-programmable gate array (FPGA), or other digital logic circuitry. Memory 32 may include multiple memories for storing a variety of data. For example, one memory may contain therapy parameters, one may contain PTD operational files, and one may contain therapy data. Memory 32 may include any one or more of a random access memory (RAM), read-only memory (ROM), electronically-erasable programmable ROM (EEPROM), flash memory, or the like.

Processor 30 may also send data to USB circuit 44 when a USB device is present to save data from therapy. USB circuit 44 may control both USB ports in the present embodiment; however, USB circuit 44 may control any number of USB ports included in PTD 14. In some embodiments, USB circuit may be an IEEE circuit when IEEE ports are used as a means for transferring data.

The USB circuit may control a variety of external devices. In some embodiments, a keyboard or mouse may be connected via a USB port for system control. In other embodiments, a printer may be attached via a USB port to create hard copies of patient data or summarize the therapy. Other types of connectivity may be available through the USB circuit 44, such as internet access.

Communications with PTD 14 may be accomplished by radio frequency (RF) communication or local area network (LAN) with another computing device or network access point. This communication is possible through the use of communication interface 80. Communication interface 46 may be configured to conduct wireless or wired data transactions simultaneously as needed by a user, e.g., a physician or clinician. In some embodiments, communication interface 46 may be directly connected to connector block 40.

PTD 14 may communicate with a variety of device to enable appropriate operation. For example, PTD may utilize communication interface 46 to monitor inventory, order disposable parts for therapy from a vendor, and download upgraded software for a therapy. In some embodiments, the physician may communicate with a help-desk, either computer directed or human staffed, in real-time to solve operational problems quickly. These problems with PTD 14 or a connected hand-held device may be diagnosed remotely and remedied via a software patch in some cases.

Screen 34 is the interface between PTD 14 and the physician. Processor 30 controls the graphics displayed on screen 34 and identifies when the physician presses on certain portions of the screen 34, which is sensitive to touch control. In this manner, screen 34 operation may be central to the operation of PTD 14 and appropriate therapy or diagnosis.

Power source 48 delivers operating power to the components of PTD 14. Power source 48 may utilize electricity from a standard 115 Volt electrical outlet or include a battery and a power generation circuit to produce the operating power. In other embodiments, power source 48 may utilize energy from any outlet that provides between 100 and 240 Volts. In some embodiments, the battery may be rechargeable to allow extended operation. Recharging may be accomplished through the 115 Volt electrical outlet. In other embodiments, traditional batteries may be used.

Figure 3:
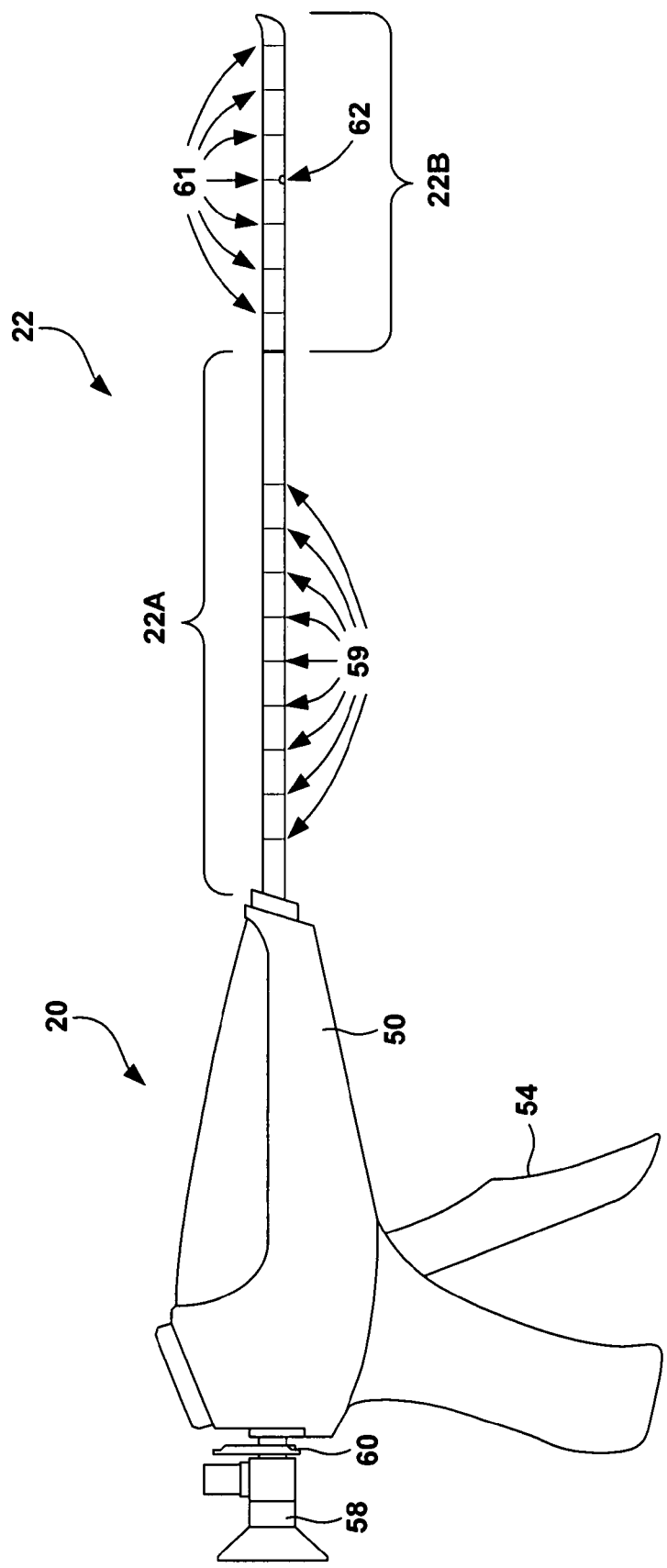
FIG. 3 is a side view of an example hand-held device with a elongated housing that includes a distal viewing window with graduations.

FIG. 3 is a side view of an example hand-held device with a elongated housing that includes a distal viewing window with graduations. As shown in FIG. 3, hand-held device 20 is shown as it would be configured and used by a user to deliver ablation therapy to patient 12. Hand-held device 20 includes housing 50, lever 54, and sliding lock 60. Cystoscope 58 and elongated housing 22 are integrated into hand-held device 20 for therapy. Elongated housing 22 includes port 62 which allows a needle electrode (not shown) to extend out of the elongated housing to treat prostate 24 of patient 12.

Elongated housing 22 includes proximal end 22A and distal viewing window 22B. As shown in FIG. 3, distal viewing window 22B resides over all sides of, or around the entire circumference of, the entire distal end of elongated housing 22. However, other examples of elongated housing 22 may include distal viewing window 22B along the length of the distal end without surrounding the entire perimeter of the housing. In other words, distal viewing window 22B may only be located along a side of elongated housing 22 while the remaining side portion, or top or bottom portion, of the distal end of the elongated housing is not configured to view adjacent tissue. In alternative examples, distal viewing window 22B may not include the distal tip if elongated housing 22.

Distal viewing window 22B allows the user to view tissue adjacent to the distal viewing window with cystoscope 58. In this manner, the user may move cystoscope 58 axially along distal viewing window 22B to view a large area of tissue without needing to move elongated housing 22 in relation to the tissue. Distal viewing window 22B may have an axial length equal to or greater than approximately 10 percent of the total elongated housing 22 length. Accordingly, proximal end 22A may have an axial length less than 80 percent of the elongated housing 22 length. More specifically, distal viewing window 22B may have an axial length between approximately 20 percent and 50 percent of the total elongated housing 22 length. In a specific example, elongated housing 22 includes proximal end 22A having a length of approximately 18 centimeters (cm) and distal viewing window 22B having a length of approximately 9 cm. In this example, distal viewing window 22B length is approximately 33 percent of the total elongated housing 22 length. Elongated housing 22 may have other lengths in alternative examples. Accordingly, the axial length of distal viewing window 22B may be of sufficient length to visualize the distance between multiple anatomical features within the body lumen of the patient. Example anatomical features may include the verumontanum, the apex of prostate 24, or the urinary sphincter. The user may desire to visualize any number of anatomical features necessary or beneficial to properly place the therapy delivered via the elongated housing.

Graduations 61 are located at spaced positions along the lengths of distal viewing window 22B. Graduations 61 may wrap around the perimeter of distal viewing window 22B to allow the user to view the graduations at any perimeter position of the distal viewing window. Accordingly, graduations 59 may wrap around the perimeter of proximal end 22A to allow the user to view the graduations outside of patient 12. Graduations 61 and 59 have equal spacing so that the user can measure the distance between port 62 and the target tissue identified through distal viewing window 22B. The user may then adjust the axial position of elongated housing 22 by using graduations 59 as markers outside of patient 12. Port 62 is the location in which the ablation needle electrode exits elongated housing 22 in order to extend into the target tissue. Graduations 59 and 61 may be created using any one of etchings in elongated housing 22, markings added to the outside of the elongated housing, or markings formed within the elongated housing. Generally, graduations 59 and 61 may have a spacing separating each graduation between approximately 0.1 cm and 3.0 cm. In the example of FIG. 3, graduations 59 and 61 have a spacing of approximately 1.0 cm.

The user, such as a clinician or physician, inserts cystoscope 58 into hand-held device 20 and the scope channel (not shown) of elongated housing 22. Cystoscope 58 includes an eye piece, a lens, and a shaft that transmits light from the lens to the eye piece to allow a user to view tissues within patient 12 via distal viewing window 22B. Once cystoscope is inserted into hand-held device 20, the user may slide sliding lock 60 to the closed (locked) position. The portion of cystoscope 58 that remains outside of hand-held device 20 and elongated housing 22 includes an eye piece that the user holds up to one eye to view the image transmitted from elongated housing 22, through cystoscope 58, and to the eye piece.

Elongated housing 22 is inserted into the urethra of patient 12 with the aid of a lubricant and local anesthetic. The user holds onto the handle of hand-held device 20 to apply axial pressure to elongated housing 22 and slide the elongated housing deeper within the urethra of patient 12. The user looks thought cystoscope 58 and out of distal viewing window 22B of elongated housing 22. The user uses cystoscope 58 to identify predetermined anatomical landmarks, such as the verumontanum, within patient 12 to find the location of prostate 24. Once elongated housing 22 is correctly positioned adjacent to prostate 24, the user may commence ablation therapy through using lever 54 and applying the selected ablation therapy. As shown, squeezing lever 54 against the handle of housing 50 forces the ablation needle electrode (not shown) to extend out of port 62 and into the target tissue. The user may push lever 54 back away from the handle to retract the ablation needle electrode once ablation therapy is complete.

In some examples, more than one ablation needle electrode may extend from elongated housing 22. Each ablation needle that is extended from distal viewing window 22B may extend out from a separate port, similar to port 62. However, multiple ablation needle electrodes may extend from the same port. Multiple ablation needle electrodes may be spaced around the circumference of elongated housing 22 and/or along the length of the elongated housing. While lever 54 may be coupled to all ablation needle electrodes, other examples of hand-held device may include multiple levers that are coupled to respective ablation needle electrodes. In this manner, the user may selectively extend an ablation needle electrode from elongated housing 22 and into patient 12.

Housing 50 and other components of hand-held device 20 may generally be constructed of metals, polymers, and composite materials. Metals used in the construction of components in hand-held device 20 may include stainless steel, aluminum, an aluminum alloy, titanium, a titanium alloy, or another metal alloy commonly used for hand-held devices. Example polymers may include nylon, polyurethane, high molecular weight polyurethane, polyethylene, polyvinylchloride, or any other polymer. In some examples, components of hand-held device 20 may include one or more different materials to satisfy aesthetic, ergonomic, or functional requirements of the device. In a preferred embodiment, components of hand-held device 20 may be constructed of molded polymers to reduce weight and cost of manufacturing the device.

Elongated housing 22 may be generally constructed of at least one metal, polymer, and composite material. Metals that may be used in the construction of elongated housing 22 may include stainless steel, aluminum, an aluminum alloy, titanium, a titanium alloy, or other metal alloys. Example polymers that may be used in the construction of elongated housing 22 may include nylon, polyurethane, high molecular weight polyurethane, polyethylene, polyvinylchloride, or any other polymer. Specifically, distal viewing window 22B may be constructed of a polymer that is at least partially transparent. For example, distal viewing window 22B may be constructed of clear polyvinyl chloride while the remaining portion of elongated housing 22 may be constructed of high molecular weight polyurethane. Elongated housing 22 may be constructed with a combination of any of these or other materials.

Elongated housing 22 may generally be rigid in axial, radial, and circumferential directions. However, a portion or the entire elongated housing 22 may be flexible in one or more dimensions. For example, elongated housing may be semi-rigid in the radial direction while remaining stiff in the axial and circumferential directions. The stiffness of elongated housing 22 may be varied depending on the configuration of elongated housing components. For example, elongated housing 22 may be rigid in order to provide sufficient resistance to torque from the extension of the ablation needle electrode into the target tissue.

Figure 4A:
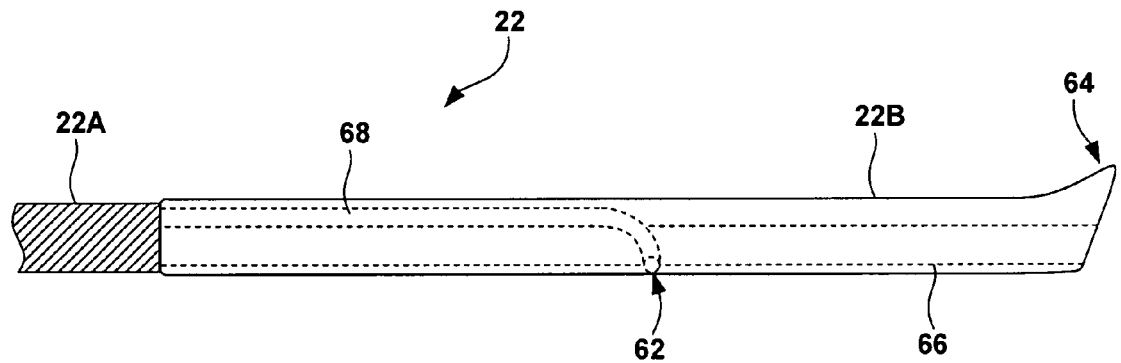
FIGS. 4A-4C are views of an example elongated housing with a distal viewing window and a port located in the middle of the viewing window.
Figure 4B:
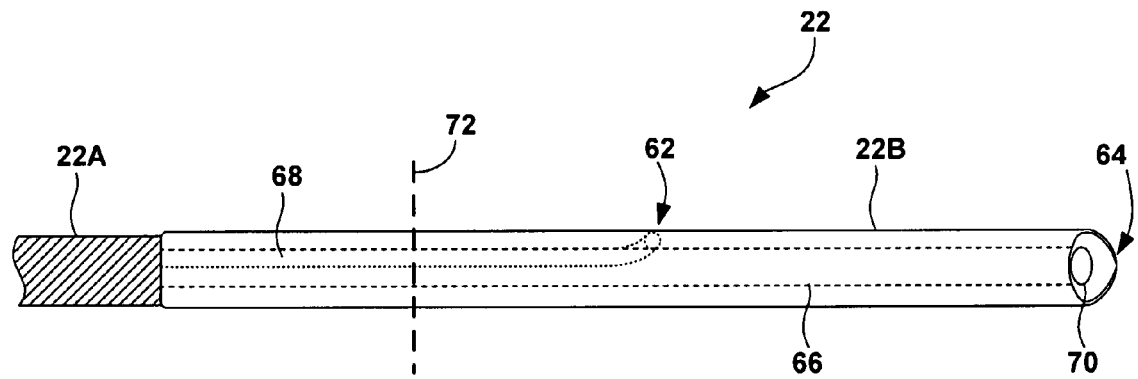
Figure 4C:
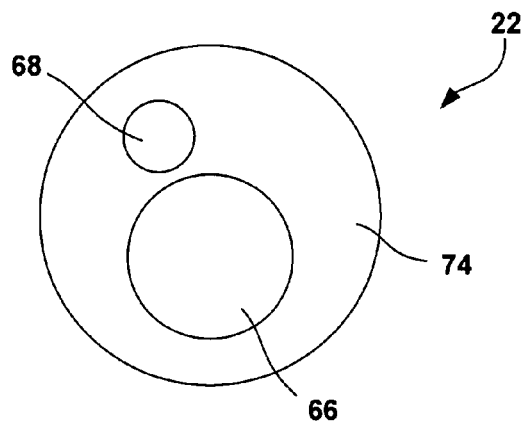

FIGS. 4A-4C are views of an example elongated housing with a distal viewing window and a port located in the middle of the viewing window. As shown in FIG. 4A, a side view of elongated housing 22 is illustrated and includes proximal end 22A and distal viewing window 22B at the distal end of the elongated housing. Distal viewing window 22B defines needle channel 68, scope channel 66, and distal tip 64. Needle channel 68 exits distal viewing window 22B through port 62 located on a side of the distal viewing window. Distal tip 64 facilitates the insertion of elongated housing 22 into the urethra of patient 12. While not shown in FIGS. 4A-4C, graduations may be provided on proximal end 22A and distal viewing window 22B, similar to FIG. 3.

Needle channel 68 is configured to accept an ablation needle electrode (not shown). In some examples, the ablation needle electrode may be covered by a sheath to separate the ablation needle electrode from the sides of needle channel 68. Needle channel 68 is oriented substantially parallel to the housing axis of elongated housing 22 until the needle channel curves to be substantially orthogonal to the housing axis where it opens to port 62. Port 62 may be a substantially circular opening in the side, or at any point around the perimeter, of distal viewing window 22B that allows the ablation needle to exit the distal viewing window of elongated housing 22. Port 62 may be generally located in the middle of distal viewing window 22B to allow the user to identify tissue proximal to or distal to the port. In this manner, distal viewing window 22B may allow the user to view tissue on either side of port 62 and reduce the number of times the user may have to adjust the position of elongated housing 22 within patient 12. In other embodiments, port 62 may be located at other middle portions of distal viewing window 22B. In general, at least 20 percent of the distal or proximal portion of distal viewing window 22B may be located distally or proximally to the port, respectively.

Scope channel 66 is configured to accept cystoscope 58 for viewing tissue adjacent to distal viewing window 22B. Scope channel 66 is oriented substantially parallel to the housing axis of elongated housing 22. Scope channel 66 is not shown to be coaxial with elongated housing 22; however, other examples of the elongated housing may have the axis of scope channel 66 coincident with the housing axis. The user may move cystoscope 58 within scope channel 66 in order to view any positions along the sides of distal viewing window 22. Moving cystoscope 58 instead of elongated housing 22 may reduce abrasion to the adjacent tissue, patient 12 pain, and procedure time.

FIG. 4B shows a bottom view of elongated housing 22. Distal tip 64 is shown as the most distal point of elongated housing 22 such that the end of the elongated housing is sloped from the distal tip. The sloped end of elongated housing 22 may allow cystoscope 58 to view tissue out of housing end 70 of the elongated housing in addition to tissue adjacent to the sides of distal viewing window 22B. Port 62 is located along an oblique side of distal viewing window 22B; however, the port may be located at any location along the axis or circumference of the distal viewing window.

In other examples of elongated housing 22, the length of the elongated housing may not be substantially straight. The length of elongated housing 22 may have one or more curves, bends, kinks, bulges, or any other shape that changes with position along the length of the elongated housing. These different shapes of elongated housing 22 may be utilized to facilitate insertion of the elongated housing into a lumen, prevent further insertion of the elongated housing, or house a specific element within the elongated housing.

FIG. 4C shows a cross-sectional view of elongated housing 22 at plane 72 of FIG. 4B. Elongated housing 22 includes window material 74 of distal viewing window 22B which defines scope channel 66 and needle channel 68. Window material 74 is shown as defining the entire structure of distal viewing window 22B. In alternative examples, the outer surface of needle channel 68 may include an additional material to insulate the ablation needle electrode from distal viewing window 22B or provide lubrication properties to the ablation needle. Additionally, distal viewing window 22B may include a surface layer that separates window material 74 from tissue of patient 12. For example, the surface layer may be a biocompatible material while window material 74 may provide optical properties desirable when identifying the adjacent tissue.

The cross-section of elongated housing 22, scope channel 66, and needle channel 68 are shown as substantially circular. However, other examples of elongated hosing 22 may have cross-sections that are not substantially circular. One or more of elongated housing 22, scope channel 66, and needle channel 68 may have a cross-sectional shape that is an oval, square, octagon, or any other polygon. Circular cross-sections may allow elongated housing 22 to rotate within the urethra, cystoscope 58 to rotate within scope channel 66, and the ablation needle electrode to rotate within needle channel 68. If rotation is not desired, non-circular cross-sections may be utilized by elongated housing 22.

Figure 5A:
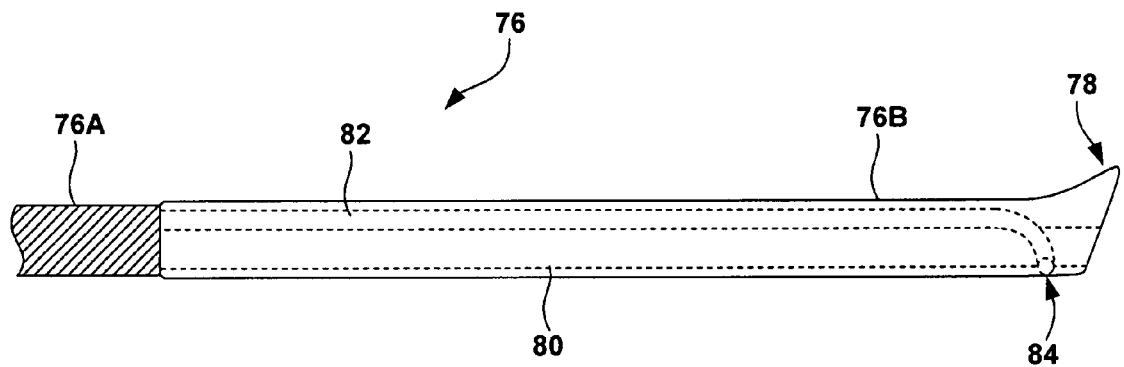
FIGS. 5A and 5B are side views of example elongated housings with a distal viewing window that includes a port located at the distal end of the viewing window or the proximal end of the viewing window.
Figure 5B:
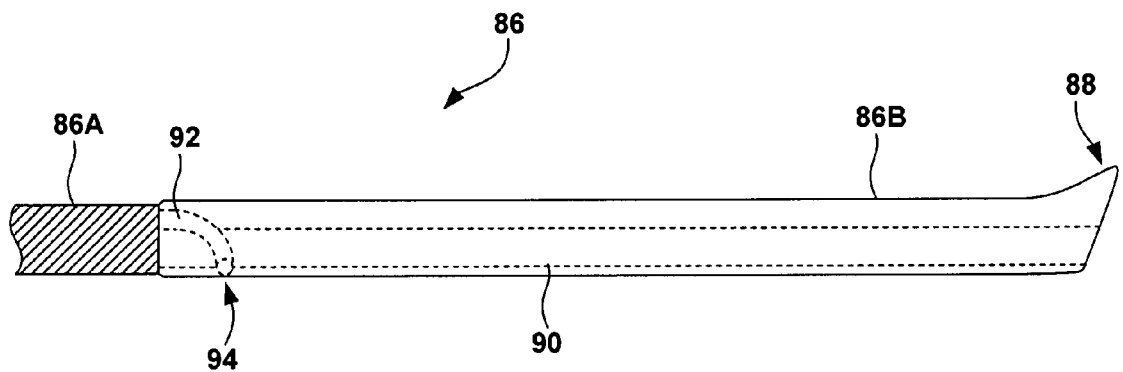

FIGS. 5A and 5B are side views of example elongated housings 76 and 86 with a distal viewing window that includes a port located at the distal end of the viewing window or the proximal end of the viewing window. Elongated housings 76 and 86 are alternative examples of similar elongated housing 22. While not shown in FIGS. 5A-5B, graduations may be provided on proximal ends 76A and 86A and distal viewing windows 76B and 86B, similar to FIG. 3. As shown in FIG. 5A, elongated housing 76 includes proximal end 76A, distal viewing window 76B, and distal tip 78. Elongated housing 76 also includes scope channel 80 and needle channel 82. Elongated housing 76 differs from elongated housing 22 in that needle channel 82 continues to a location near the distal end of distal viewing window 76B. Needle channel 82 curves toward the side of distal viewing window 76B and exits out of port 84. Port 84 is located near the distal end of elongated housing 76 to prevent unnecessary insertion of the elongated housing further into the urethra. Distal viewing window 76B allows the user to determine of port 84 has been advanced too far into the urethra.

As shown in the example of FIG. 5B, elongated housing 86 includes proximal end 86A, distal viewing window 86B, and distal tip 88. Elongated housing 86 also includes scope channel 90 and needle channel 92. Elongated housing 86 differs from elongated housing 22 in that needle channel 92 ends at a location near the proximal end of distal viewing window 86B. Needle channel 92 curves toward the side of distal viewing window 86B and exits out of port 94 near proximal end 86A. Port 94 is located near proximal end 86A of elongated housing 86 to identify the target tissue via distal viewing window 86B before elongated housing 86 is inserted fully into the urethra. In this manner, elongated housing may be correctly positioned with one initial movement into patient 12 and a second movement into patient 12 based upon identification of the target tissue through distal viewing window 86B.

Figure 6A:
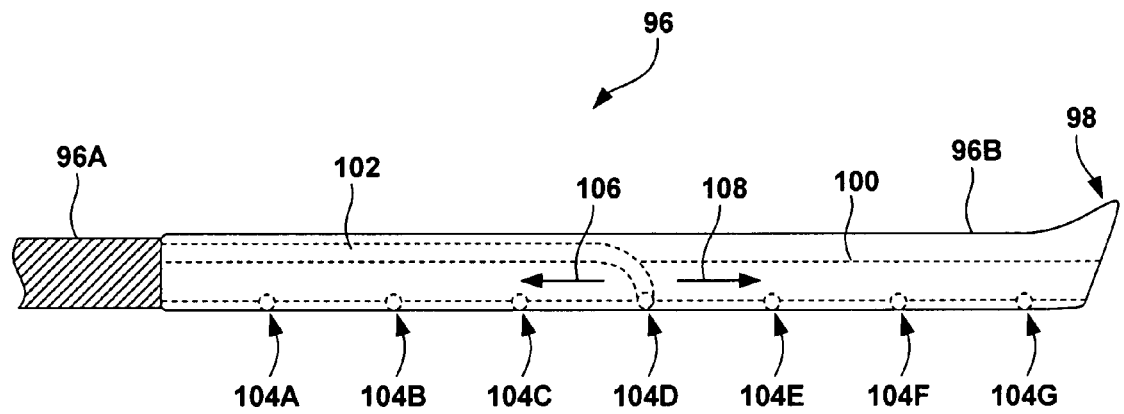
FIGS. 6A and 6B are side views of an example elongated housing with a distal viewing window that includes a needle channel slidable within with elongated housing.
Figure 6B:
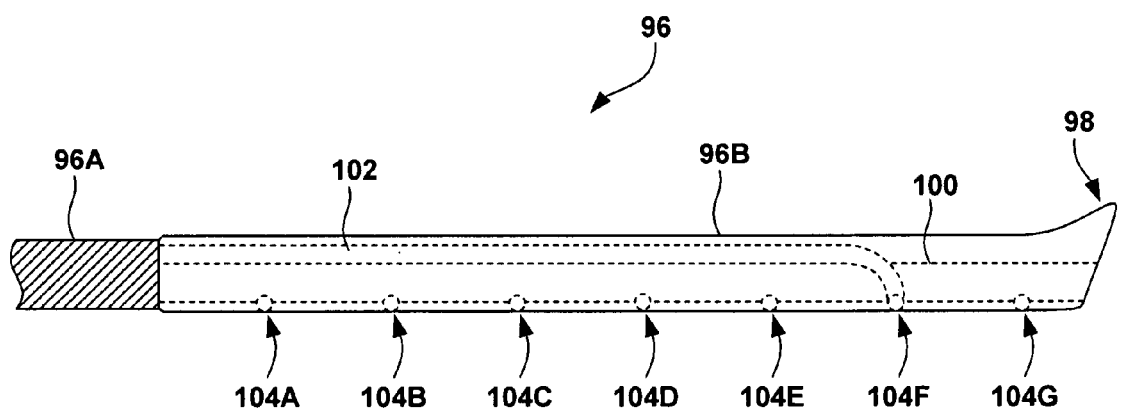

FIGS. 6A and 6B are side views of an example elongated housing 96 with a distal viewing window that includes a needle channel slidable within the elongated housing. While not shown in FIGS. 6A-6B, graduations may be provided on proximal end 96A and distal viewing window 96B, similar to FIG. 3. As shown in FIG. 6A, elongated housing 96 includes proximal end 96A, distal viewing window 96B, and distal tip 98. Elongated housing 96 also includes scope channel 100 and needle channel 102. Elongated housing 96 differs from elongated housing 22 in that needle channel 102 is movable within distal viewing window 96B. Needle channel 102 may be moved to exit out of any one of ports 104A-104G (collectively "ports 104"). Initially, needle channel 102 may be positioned to exit out of port 104D.

Elongated housing 96 also includes ports 104 positioned along the length of distal viewing window 96B. Needle channel 102 and ports 104 allow the user to treat any target tissue adjacent to distal viewing window 96B without moving elongated housing 96 relative to the urethra. The user may move needle channel 102 axially in the direction of either arrow 106 or 108, depending on the location of the target tissue in relation to the present location of the needle channel. Needle channel 102 is positioned such that the needle channel exits out of the desired one of ports 104 and the ablation needle electrode (not shown) can exit from elongated housing 96 and extend into the target tissue. The user may move needle channel 102 via a lever, button, knob, or other device on hand-held device 20 or proximal end 96A that is accessible to the user during therapy.

Each one of ports 104 may be aligned with one of the plurality of graduations that help the user position elongated housing 96 within patient 12. Alternatively, ports 104 may be provided within the graduations such that the user can identify the desired port to align with needle channel 102. While seven ports 104 are shown in the example of FIG. 6A, other examples of elongated housing 96 may include more or less ports within distal viewing window 96B. In addition, elongated housing 96 may include multiple ports at two or more circumferential locations around the perimeter of distal viewing window 96B. In this case, needle channel 102 may move to different circumferential positions within elongated housing 96 or the elongated housing may have one needle channel for each set of ports at the same circumferential position of the elongated housing. These alternative embodiments may allow the user to access target tissues located around distal viewing window 96B without rotating elongated housing 96 relative to the urethra.

FIG. 6B illustrates an alternative embodiment that includes elongated housing 96 with needle channel 102 moved toward the distal end of the elongated housing to exit out of port 104F. In this configuration, elongated housing 96 is ready to extend the ablation needle electrode out of needle channel 102 and port 104F and into the target tissue. After ablation energy has been delivered to the target tissue via port 104G, the user may continue therapy by moving needle channel 102 to a different one of ports 104, extending the needle electrode, and delivering ablation energy again. The user may continue this process until ablation therapy is complete for patient 12. In this manner, the user is able to create multiple lesions within patient 12 without constantly moving elongated housing 96 against the urethra of the patient.

Figure 7:
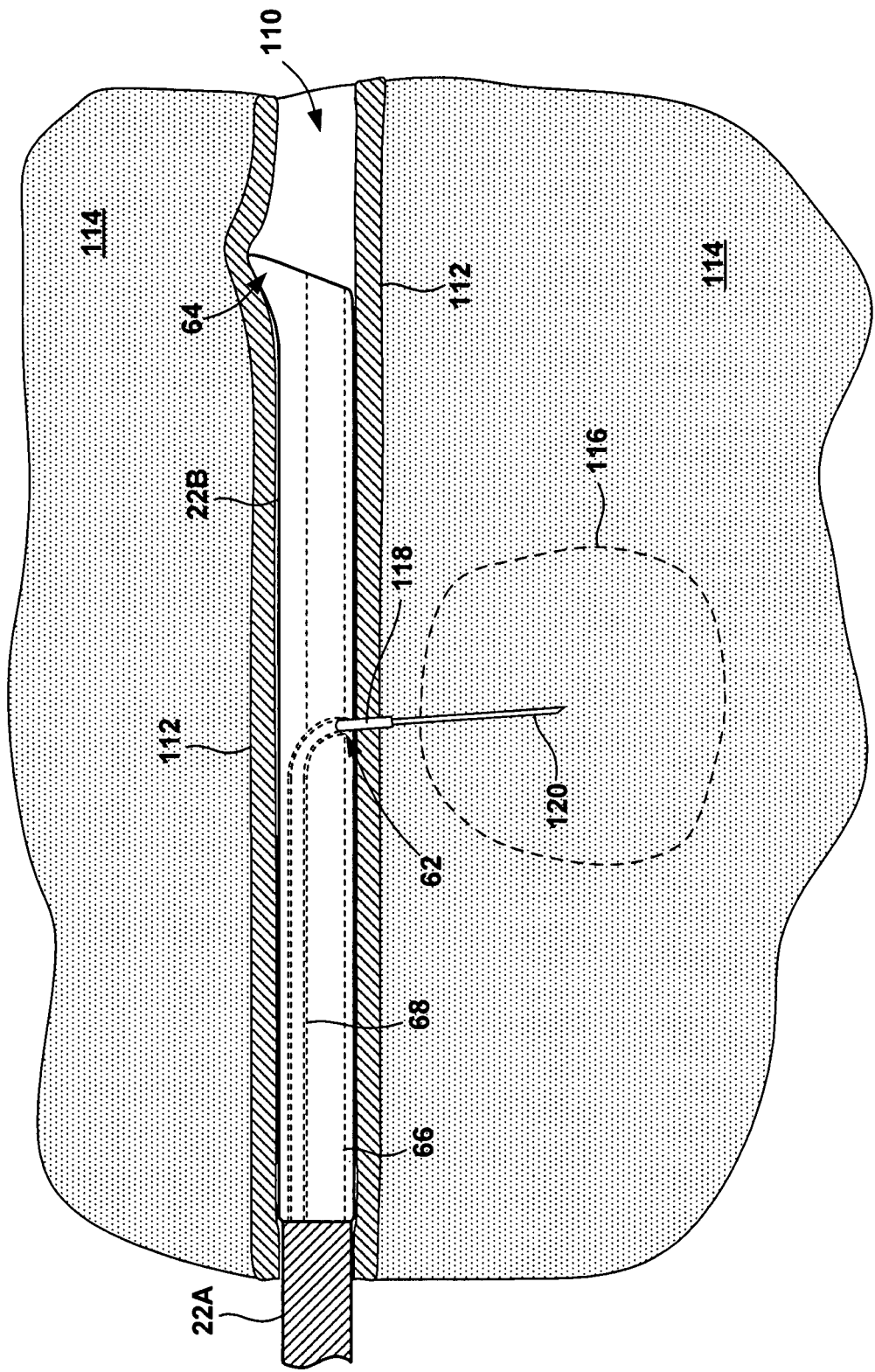
FIG. 7 is a conceptual diagram illustrating an example elongated housing within the urethra of a patient with the ablation needle electrode extended into the target tissue.

FIG. 7 is a conceptual diagram illustrating an example elongated member 22 within the urethra of a patient with the ablation needle electrode extended into the target tissue. While elongated member 22 is shown in the example of FIG. 7, any of elongated members 76, 86 and 96 may be utilized in the ablation therapy procedure. As shown in FIG. 7, elongated member 22 is inserted into urethra 110 and against urethra wall 112. Distal viewing window 22B is positioned adjacent to tissue 114, and more specifically, target tissue 116. Target tissue 116 may be within prostate 24 of patient 12 when performing prostate ablation therapy. Distal tip 64 was used to initially insert elongated member 22 into urethra 110.

Distal viewing window 22B has been used to identify surrounding tissue and the location of target tissue 116. For example, the user may have used cystoscope 58 within scope channel 66 to identify the verumontanum. The user then positioned elongated housing 22 such that port 62 is located in proximity to target tissue 116. Once elongated housing 22 has been correctly positioned, the user extends ablation needle electrode 120 out of needle channel 68 and port 62 until the ablation needle electrode has penetrated through urethra 112 and into the desired depth of target tissue 116. Ablation therapy may be started once ablation needle electrode 120 is positioned within target tissue 116. During ablation, fluid may be used to flush debris out of urethra 110 and cool urethra wall 112. In other examples, a conductive fluid may be delivered out of ablation needle electrode 120 or elongated housing 22 to create a larger effective electrode surface area within target tissue 116.

Ablation needle electrode 120 is surrounded by sheath 118 that insulates the ablation needle electrode from needle channel 68. Sheath 118 may also aid in controlling ablation energy delivered to target tissue 116 by how much of ablation needle electrode 120 is covered by the sheath. In addition, target tissue 116 may be treated by extending ablation needle electrode 120 into multiple locations of the target tissue. This approach may be necessary to treat large target tissue areas or prevent long durations of delivered ablation energy to patient 12.

Figure 8:
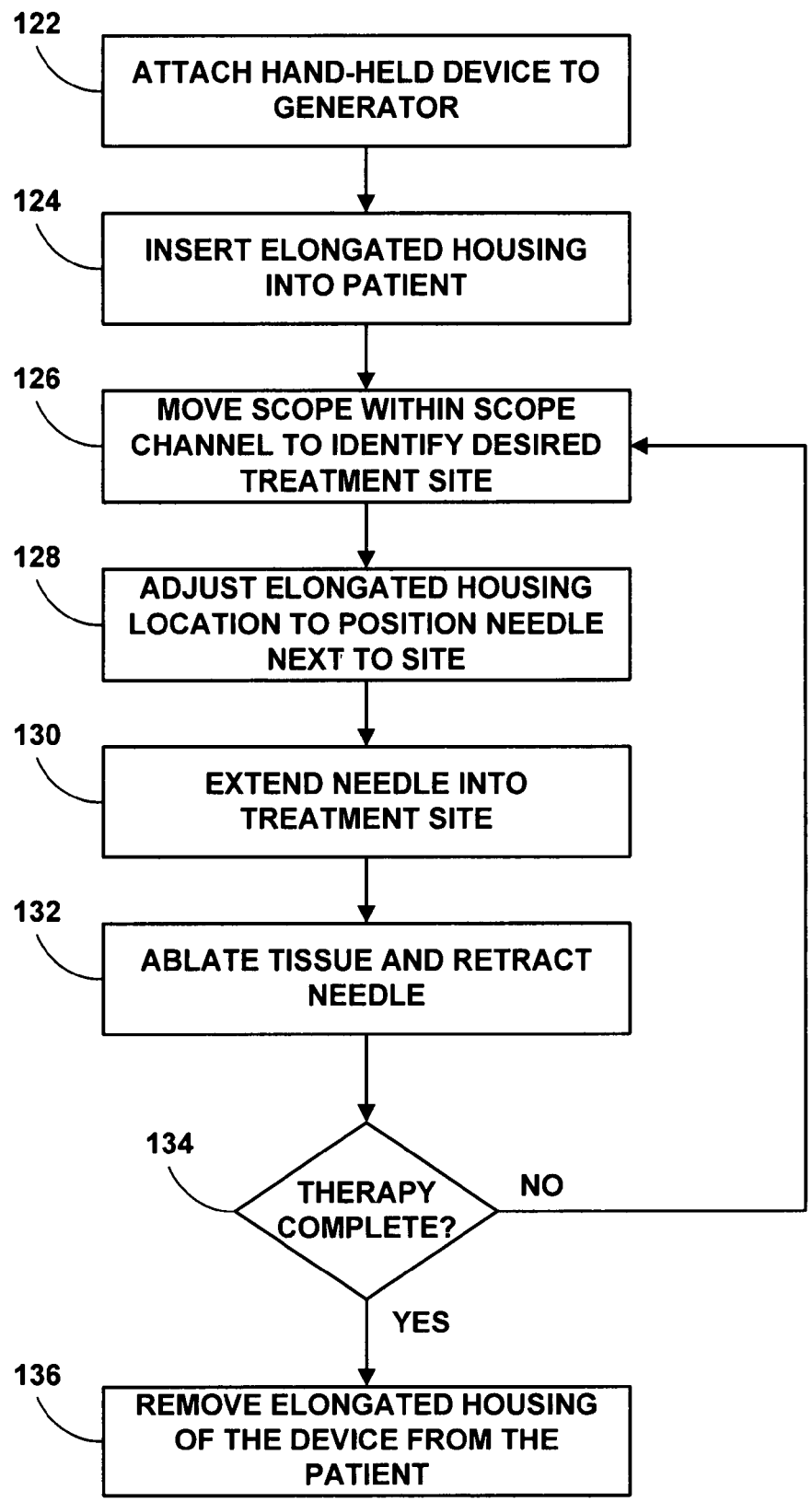
FIG. 8 is a flow diagram illustrating an example technique for positioning an elongated housing within a lumen with the distal viewing window and delivering therapy to the target tissue.

FIG. 8 is a flow diagram illustrating an example technique for positioning an elongated housing within a lumen with the distal viewing window and delivering therapy to the target tissue. Hand-held device 20 and elongated housing 22 will be used in the example of FIG. 8; however, any of elongated housings 76, 86 and 96 may be used in a similar manner to perform the ablation therapy. Initially, the user attaches hand-held device 20 to PTD 14 (a generator) with cable 16 and tube 18 (122). Once system 10 is ready for insertion into patient 12, the user slides elongated housing 22 into the urethra of the patient until the elongated housing is estimated to be positioned correctly adjacent to prostate 24 (124).

The user then moves cystoscope 58 within scope channel 66 to identify the target tissue for ablation via distal viewing window 22B (126). For example, the user may look to identify the location of the verumontanum as a landmark for positioning port 62. After identifying target tissue 116, the user adjusts the elongated housing position within the urethra to correctly position port 62 adjacent to the target issue site (128). The user then extends ablation needle electrode 120 into urethra wall 112 and target tissue 116 (130) before delivering ablation energy to the target tissue and subsequently retracting the ablation needle electrode. If the ablation therapy is not complete (134), the user repeats the procedure by identifying the next target tissue site via distal viewing window 22B (126). If ablation therapy is complete (134), the user removes elongated housing 22 from patient 12 (136).

Hand-held device 20 and any of elongated housings 22, 76, 86 and 96 may be restricted for use with only one patient to prevent the transmission of disease between patients. Elongated housing 22 and/or hand-held device 20 may be disposed of immediately after use. Alternatively, elongated housing 22 may be disposed while hand-held device 20 is sterilized before being used with a different patient. In any event, elongated housing 22 may be configured to be disposable or sterilized as desired by user 20.

Elongated housings 22, 76, 86 and 96 have been described herein as being used for the extension of a needle electrode for prostate ablation therapy. However, any elongated housing may be used for other ablation therapies including, but not limited to, cardiac ablation therapy, brain tissue therapy, surgical ablation cutting, or surgical cautery.

The preceding specific embodiments are illustrative of the practice of the invention. It is to be understood, therefore, that other expedients known to those skilled in the art or disclosed herein may be employed without departing from the invention or the scope of the claims. Many embodiments of the invention have been described. Various modifications may be made without departing from the scope of the claims. These and other embodiments are within the scope of the following claims.

The invention claimed is:

1. A medical device comprising:
  an elongated housing that defines a scope channel, a needle channel, and a distal viewing window, the scope channel being configured to receive a scope for viewing patient tissue adjacent to the distal viewing window, wherein:
  the distal viewing window is located near a distal end of the elongated housing;
  the distal viewing window is at least partially transparent and located along a window axial length and around a portion of a housing perimeter; and
  the distal viewing window has a length that is between 20 percent and 50 percent of a housing length;
  a plurality of ports at respective axial locations in the distal viewing window, wherein the needle channel is movable axially within the elongated housing to allow the needle channel to align axially with and open to any of the plurality of ports; and
  a needle that resides within the needle channel and is configured to exit out of any of the plurality of ports in the distal viewing window.

2. The medical device of claim 1, further comprising:
  a plurality of window graduations located over the distal viewing window; and
  a plurality of housing graduations located over a proximal end of the elongated housing.

3. The medical device of claim 2, wherein the plurality of window graduations have a first spacing equal to a second spacing of the plurality of housing graduations.

4. The medical device of claim 1, wherein the viewing window is located around an entire housing perimeter.

5. The medical device of claim 1, wherein:
the scope channel is parallel to an elongated housing axis of the elongated housing and accepts a cystoscope that is inserted into the scope channel; and
the needle channel is substantially parallel to an elongated housing axis.

6. The medical device of claim 1, wherein the needle channel is configured to open to each one of the plurality of ports in the distal viewing window.

7. The medical device of claim 1, wherein at least 20 percent of the distal viewing window is located distally of all of the plurality of ports.

8. The medical device of claim 1, further comprising a distal tip attached to the elongated housing that extends away from an elongated housing axis and the distal end.

9. The medical device of claim 1, wherein the needle channel is oriented substantially parallel to an axis of the elongated housing until the needle channel curves to be substantially orthogonal to the axis at one of the plurality of the ports.

10. The medical device of claim 1, wherein the elongated housing is rigid.

11. A system comprising:
a hand-held device comprising a lever actuated by a user;
an elongated housing coupled to the hand-held device that defines a scope channel, a needle channel, and a distal viewing window, the scope channel being configured to receive a scope for viewing patient tissue adjacent to the distal viewing window, wherein:
the distal viewing window is located near a distal end of the elongated housing;
the distal viewing window is at least partially transparent and located along a window axial length and around a portion of a housing perimeter; and
the distal viewing window has a length that is between 20 percent and 50 percent of a housing length;
the elongated housing comprises a plurality of ports at respective axial locations in the distal viewing window; and
the needle channel is movable axially within the elongated housing to allow the needle channel to align axially with and open to any of the plurality of ports; and
an ablation needle electrode that resides within the needle channel and exits out of one of the plurality of ports in the distal viewing window in response to actuation of the lever.

12. The system of claim 11, further comprising a cystoscope having a lens and an eyepiece, wherein the cystoscope is inserted into the scope channel to transmit light from the distal viewing window, through the lens, and to the eyepiece.

13. The system of claim 11, further comprising a generator that produces radio frequency ablation energy, wherein the ablation needle electrode delivers the radio frequency ablation energy to a tissue of patient.

14. The system of claim 11, wherein the elongated housing comprises:
a plurality of window graduations located over the distal viewing window; and
a plurality of housing graduations located over a proximal end of the elongated housing.

15. The system of claim 11, wherein the viewing window is located around an entire housing perimeter.

16. The system of claim 11, wherein:
the scope channel is parallel to an elongated housing axis of the elongated housing; and
the needle channel is substantially parallel to the elongated housing axis.

17. The system of claim 11, wherein at least 20 percent of the distal viewing window is located distally of the plurality of the ports.

18. The system of claim 11, wherein the needle channel is oriented substantially parallel to an axis of the elongated housing until the needle channel curves to be substantially orthogonal to the axis at one of the plurality of the ports.

19. The system of claim 11, wherein the elongated housing is rigid.

20. A method comprising:
inserting an elongated housing that defines a scope channel, a needle channel, and a distal viewing window into a lumen of a patient, wherein:
the distal viewing window is located near a distal end of the elongated housing;
the distal viewing window is at least partially transparent and located along a window axial length and around a portion of a housing perimeter; and
the window axial length is between 20 percent and 50 percent of a housing length;
moving a cystoscope axially within the scope channel;
identifying a target tissue through the distal viewing window via the cystoscope; and
moving the needle channel axially within the elongated housing in order for the needle channel to align axially with and open to one of a plurality of ports in the distal viewing window adjacent to the target tissue, each of the plurality of ports at respective axial locations in the distal viewing window, wherein a needle resides within the needle channel and is configured to exit out of the one of the plurality of ports in the distal viewing window.

21. The method of claim 20, further comprising:
positioning the elongated housing within the lumen with respect to the target tissue; and
delivering ablation therapy to the target tissue of the patient.

22. The method of claim 21, wherein the needle is an ablation needle electrode, and wherein delivering ablation therapy comprises:
inserting the ablation needle electrode from the needle channel into the target tissue via the one of the plurality of ports in the distal viewing window; and
heating the target tissue with radio frequency ablation energy.

23. The method of claim 22, wherein inserting the ablation needle electrode further comprises extending the ablation needle electrode from the one of the plurality of ports located proximal to at least a distal 10 percent of the distal viewing window.

24. The method of claim 20, wherein the needle is an ablation needle electrode, and wherein the method further comprises;
inserting the ablation needle electrode from the needle channel into the target tissue via one of the plurality of ports adjacent to the target tissue.

25. The method of claim 20, wherein inserting the elongated housing comprises inserting the elongated housing into a urethra of the patient, and wherein the elongated housing is rigid.

* * * * *